US00PP11604P

United States Patent [19]

Easton

[11] Patent Number: Plant 11,604

[45] **Date of Patent: *Oct. 31, 2000**

[54] APPLE TREE NAMED 'MARIRI RED'

[76] Inventor: David Easton, 'Mariri' R.D.2, Upper Moutere, Nelson, New Zealand

[ * ] Notice: This patent issued on a continued prosecution application filed under 37 CFR 1.53(d), and is subject to the twenty year patent term provisions of 35 U.S.C. 154(a)(2).

[21] Appl. No.: 08/980,181

[22] Filed: Nov. 26, 1997

Related U.S. Application Data

[63] Continuation of application No. 08/690,608, Jul. 31, 1996, abandoned.

[51] Int. Cl.[7] ..... A01H 5/00

[52] U.S. Cl. ..... Plt./161

[58] Field of Search ..... Plt./34.1, 161, Plt./174

[56] References Cited

U.S. PATENT DOCUMENTS

P.P. 7,526 5/1991 Hill et al. ..... Plt./34.1
P.P. 11,226 2/2000 Turner ..... Plt./161

OTHER PUBLICATIONS

GTITM UPOVROM Listing for NZPBR APPO74, for 'Mariri Red' Application on Apr. 29, 1991, Publication on Jul. 7, 1991.

*Primary Examiner*—Howard J. Locker
*Attorney, Agent, or Firm*—Quarles & Brady LLP

[57] ABSTRACT

The new and distinct variety of apple tree, *Malus domestica,* is a naturally occurring limb mutation of the 'Braeburn' apple tree (an unprotected New Zealand variety). The fruit of the apple tree of the new variety is characterized by highly colored dark red fruit. Unlike the parent variety, the fruit has a dark red coloration in a solid blush pattern typically covering 100% of the fruit surface. The new variety has been named 'Mariri Red'.

1 Drawing Sheet

BACKGROUND

This is a continuation of application Ser. No. 08/690,608, filed Jul. 31, 1996 (now abandoned).

A variety of apple commonly grown in New Zealand is known as 'Braeburn', which is an unpatented variety. The fruit of the 'Braeburn' apple tree is variegated in color with the typical fruit having a typical coverage of 40% to 50% red stripes. Other sports or mutants arising on trees of 'Braeburn' are similar in habit and yield to 'Braeburn' but yield fruit having a greater coverage of red over the surface area of the fruit. One variety derived from 'Braeburn', known as 'Hidala' (U.S. Plant Pat. No. 7,526) has a coverage of 50% to 70% red stripes, while another variety known as 'Joburn' (United States Plant Patent application Ser. No. 08/979898 (now abandoned) exhibits fruit with 100% dark stripes over a red blush.

SUMMARY OF THE INVENTION

The new variety, which is a naturally occurring limb mutation (sport) of 'Braeburn' was discovered in 1990, in the inventor's orchard in Nelson, New Zealand. The mutation was first noticed by the inventor 2 weeks before harvest time because 2 apples on a spur had much higher red coloration than the rest of the crop on the tree. At harvest time the difference in coloration had become even more pronounced.

In the summer of 1991, budwood was taken and budded onto MM106 rootstock. This resulted in 80 trees planted on the owner's property, located as aforesaid, in 1992. From these trees a further 440 trees were asexually propagated and planted on the owner's property in 1993. Such asexual propagation has conclusively shown that the unique combination of plant characteristics and distinctive fruit coloration characteristics come true to form and are established and faithfully transmitted through succeeding generations.

In Hawkes Bay, New Zealand, 'Mariri Red' ripens one week after 'Braeburn' and 'Hidala' and at the same time as 'Joburn', as determined by measurements of the background color, flesh firmness, titratable acidity, soluble solids (sugars) and starch levels in the fruit. This ripening time has been documented by independent reports; Fenemor, Sports Comparison Trial-Braeburn Sports, Report PH95/G/N-2 to ENZA New Zealand (International) Ltd. (1996) and Bensley, Braeburn Sports Comparison Trial, Report PH95/7/H to ENZA New Zealand (International) Ltd. (1996).

Figure 1:
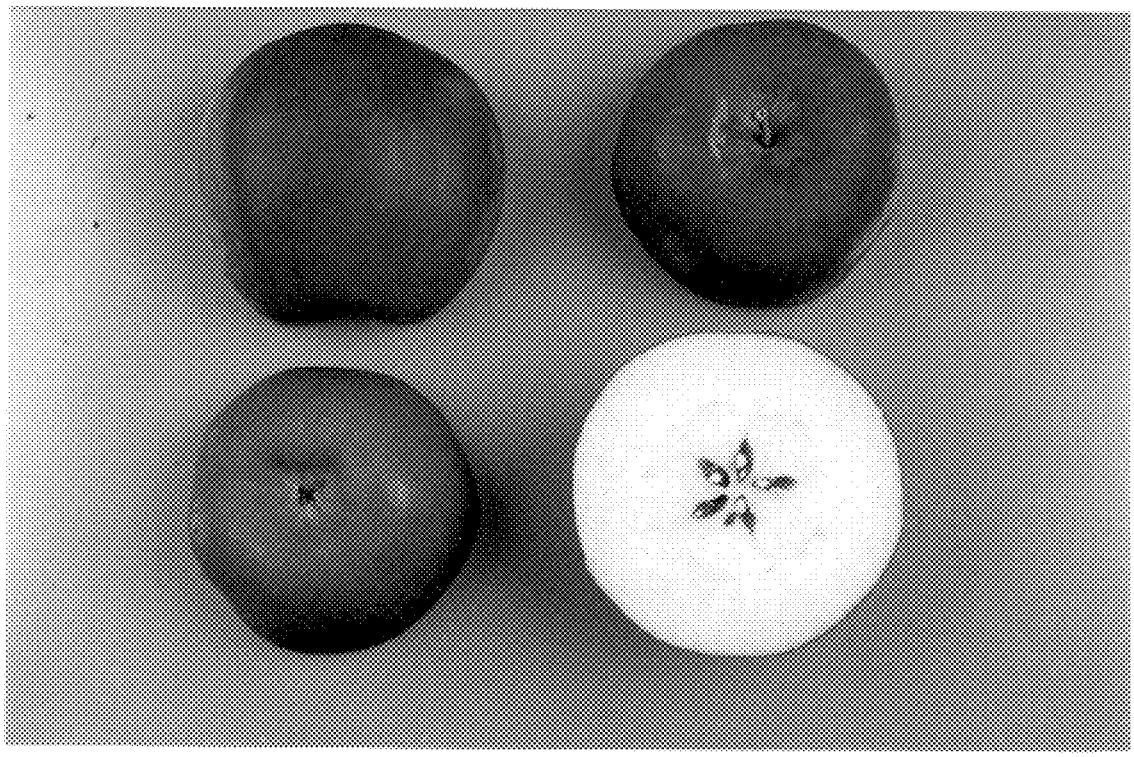
FIG. 1 shows the dark red, uniform coloration of 'Mariri Red' fruit from the stem-end, side-view, and calyx-end, as well as a cross sectional view.
Figure 2:
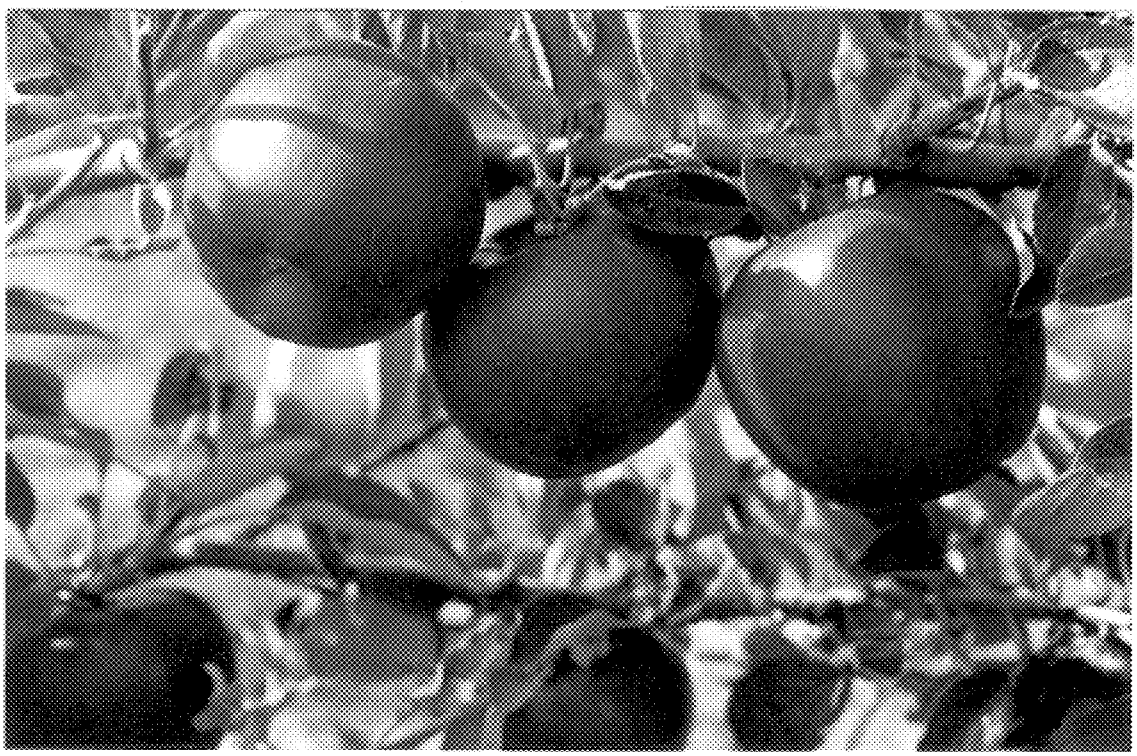
FIG. 2. shows the fruit and foliage of the 'Mariri Red' apple tree.

Colors depicted therein are as close to true as is reasonably possible to attain in color reproductions of this type.

DETAILED BOTANICAL DESCRIPTION OF THE PLANT

The trees described are growing in Havelock North, Hawkes Bay, New Zealand. Observations on trees and fruit were made in autumn 1996 on three year old trees on MM106 rootstock unless otherwise stated. Color measurements were made using The Royal Horticultural Society Colour Chart.

Tree: Medium to medium-weak vigor (on MM106 rootstock), predominance of bearing on spurs. Not substantially different from comparative varieties 'Joburn' and 'Braeburn'.

Tree size: 3.5 meters high by 2 meters wide at maturity on MM106 rootstock.

Disease resistance: Not substantially different from the comparative varieties 'Joburn' and 'Braeburn'.

Tree figure:Spreading to weeping.

Trunk: Medium stocky, smooth.

Branches: Medium thick, smooth, multi-branching.

*Color of bark.*—Brown Group 200B on one year old wood, mature wood is Grey Group 201C. Not substantially different from comparative varieties 'Joburn' and 'Braeburn'.

*Pubescence on upper half of dormant one year old shoots.*—Strong.

*Lenticels.*—Few in number (about 5 per square centimeter on one year old branches, round to ovate in shape, Greyed-White Group 156D in color. Not substantially different from comparative varieties 'Joburn' and 'Braeburn'.

*Angle of major scaffold branches.*—Typically about 60 degrees.

Foliage: Upward pose, Upper side medium glossy, strong pubescence on lower side, medium petiole length (about 27 mm).

*Leaf size.*—Width average about 42 mm, length about 67 mm.

*Leaf coloration.*—Upper surface Green Group 137A, lower surface Green Group 138B.

Flowers: Medium in size, flat in shape, petal margins touch.

*Color.*—Red-Purple Group 63B (just after opening).

*Time of flowering.*—Measured at 90% full bloom, 'Mariri Red', 'Joburn', 'Hidala', and 'Braeburn' all showed 90% full bloom at about July, 1997, at Havelock North, New Zealand.

*Sepals.*—Short to medium in length, touching at base.

Fruit: Ripens one week after 'Braeburn', late March to early April in Hastings, Hawkes Bay. Late season. The development of color begins earlier than 'Braeburn', and the color of the fruit is greater than that of 'Braeburn'. Ripeness of the fruit as determined by measurements of background color, flesh firmness, titratable acidity, soluble solids (sugars) and starch levels show that the fruit is ready for harvest one week later than 'Braeburn'.

*Size.*—Typical fruit at maturity on trees thinned in a commercial manner is about 79 mm maximun width and 65 mm in height.

*Shape.*—Short globose conical, asymmetric in side view, ribbing present, medium crowning at distil end.

*Stalk cavity.*—Medium in depth and width.

*Eye basin.*—Shallow to medium in depth, medium width (silimar to Golden Delicious).

*Bearing characteristics.*—Not substantially different from the comparative varieties. Unthinned trees tend to bear biennially, but trees thinned and cropped in a commercial manner are not biennial. Typical commercial production in New Zealand from trees grown on MM106 rootstock is about 100–150 kilograms per tree per year.

*Stem thickness.*—Medium (similar to Cox's Orange Pippin).

*Stem length.*—About 18 mm (not substantially different from the comparative varieties).

*Calyx.*—Half open. Medium in size (similar to Cox's Orange Pippin).

*Skin.*—Medium to thick, smooth, no bloom present, no greasiness present, no tendency to crack. Ground color—Yellow-Green Group 150C. Over Color—Dark red coloration (Greyed-Purple Group 187B) on a solid blush pattern typically covering 100% of fruit surface. Russeting—Low to medium amount around stem cavity. Lenticels—Small to medium in size.

*Flesh.*—Juicy, firm, Yellow-Green Group 150C, medium browning of flesh (one hour after cutting with stainless steel knife).

*Flesh texture.*—Medium (as for Cox's Orange Pippin).

*Core.*—Distinctness of core line in crosss section (median through locules) is strong. Aperture of locules in cross-section is closed.

*Seeds.*—Greyed-Orange Group 175B in color, medium in size.

*Use.*—Dessert.

*Keeping quality.*—Excellent, with fruit storing in excess of 100 days in cold storage (at 1 degree C) with few storage disorders. 'Mariri Red' fruit is not substantially different from the fruit of the comparative cultivars in this respect.

FRUIT COMPARISONS:

| | 'Mariri Red' | 'Joburn' | 'Hidala' | 'Braeburn' |
|---|---|---|---|---|
| Overcolor (RHS) | 187B | 185A | 179A | 179A |
| Color coverage | 100% | 100% | 50–70% | 40–50% |
| Color pattern | blushed | striped over lighter blush | striped over lighter blush | striped |
| Time of ripeness | 7 days after 'Braeburn' | 7 days after 'Braeburn' | Same as 'Braeburn' | — |
| Lenticels | Same as 'Braeburn' | Same as 'Braeburn' | Same as 'Braeburn' | inconspicuous |

DIFFERENCES FROM SIMILAR VARIETIES

The varieties most similar to 'Mariri Red' are 'Braeburn' and the 'Braeburn' sport 'Joburn'.

As compared to 'Braeburn', the fruit of 'Mariri Red' has a higher amount of red coloration as it covers 100% of the fruit surface, whereas the amount of red coloration of standard 'Braeburn' normally covers about 40% to 50% of the fruit. The fruit of 'Mariri Red' has a darker red (187B) uniform blush pattern while the coloration of standard 'Braeburn' consists of a lighter (185A) red striped pattern. Fruit of 'Mariri Red' exhibit a more consistent coverage of dark red coloration throughout the tree at optimum maturity as compared to that of standard 'Braeburn' where fruit coloration varies according to relative position on the tree, with exposed fruit being the most colored, while fruit toward the tree interior remain quite pale.

As compared to 'Joburn', the fruit of 'Mariri Red' has a much darker red coloration (187B) as compared to the lighter red coloration (185A) of 'Joburn'. The fruit of 'Mariri Red' has a solid, uniform coloration whereas 'Joburn' has a pattern consisting of stripes and blush.

I claim:

1. A new and distinct variety of apple tree, which is a sport of the 'Braeburn' variety, substantially as herein described and illustrated, and which is characterized particularly by the dark red coloration which extends over the entire surface of the fruit.

* * * * *